United States Patent
Liu et al.

(10) Patent No.: US 10,575,988 B2
(45) Date of Patent: *Mar. 3, 2020

(54) OPHTHALMIC DOCKING SYSTEM WITH 3-DIMENSIONAL AUTOMATIC POSITIONING USING DIFFERENTIAL RF COUPLING

(71) Applicant: OPTIMEDICA CORPORATION, Santa Ana, CA (US)

(72) Inventors: Harvey I. Liu, Fremont, CA (US); John P. Beale, San Jose, CA (US); Jose L. Garcia, Fremont, CA (US)

(73) Assignee: AMO DEVELOPMENT, LLC, Santa Ana, CA (US)

( * ) Notice: Subject to any disclaimer, the term of this patent is extended or adjusted under 35 U.S.C. 154(b) by 127 days.

This patent is subject to a terminal disclaimer.

(21) Appl. No.: 15/782,759

(22) Filed: Oct. 12, 2017

(65) Prior Publication Data

US 2019/0110920 A1 Apr. 18, 2019

(51) Int. Cl.
*A61F 9/008* (2006.01)
*A61F 9/009* (2006.01)
(Continued)

(52) U.S. Cl.
CPC .............. *A61F 9/008* (2013.01); *A61B 90/98* (2016.02); *A61F 9/009* (2013.01);
(Continued)

(58) Field of Classification Search
CPC .............................................. A61B 2005/105
See application file for complete search history.

(56) References Cited

U.S. PATENT DOCUMENTS 4,629,989 A * 12/1986 Riehl .................... A61B 5/0555
324/300
5,463,669 A * 10/1995 Kaplan ..................... A61B 6/08
378/170
(Continued)

FOREIGN PATENT DOCUMENTS

JP 2016193028 A 11/2016

OTHER PUBLICATIONS

Fulda et al. "Alignment sensing for optical cavities using radio-frequency jitter modulation" Applied Optics vol. 56, No. 13/ May 1, 2017 (pdf attached) (Year: 2017).*
(Continued)

*Primary Examiner* — Michael W Kahelin
*Assistant Examiner* — Shirley X Jian
(74) *Attorney, Agent, or Firm* — Johnson & Johnson Surgical Vision, Inc.

(57) ABSTRACT

An RF (radio frequency) positioning system and related method for automated or assisted eye-docking in ophthalmic surgery. The system includes an RF detector system on a laser head and an RFID tag on a patient interface to be mounted on the patient's eye. The detector system includes four RF antennas located on a horizontal plane for detecting RF signals from the RFID tag, where one pair of antennas are located along the X direction at equal distances from the optical axis of the laser head and another pair are located along the Y direction at equal distances from the optical axis. Based on relative strengths and phase difference of the RF signals detected by each pair of antennas, the RF detector system determines whether the patient interface is centered on the optical axis. The RF detector system controls the laser head to move toward the patient interface until the latter is centered on the optical axis.

19 Claims, 2 Drawing Sheets

(51) Int. Cl.
*A61B 90/98* (2016.01)
*A61B 17/00* (2006.01)
*A61B 34/20* (2016.01)

(52) U.S. Cl.
CPC .............. *A61B 2017/00477* (2013.01); *A61B 2034/2051* (2016.02); *A61F 2009/00846* (2013.01); *A61F 2009/00855* (2013.01)

(56) References Cited

U.S. PATENT DOCUMENTS

| | | | | |
|---|---|---|---|---|
| 6,758,845 | B1* | 7/2004 | Weckwerth | A61B 18/203 606/9 |
| 6,927,860 | B2* | 8/2005 | Podoleanu | A61B 3/102 356/479 |
| 7,390,089 | B2* | 6/2008 | Loesel | A61F 9/008 351/208 |
| 7,817,908 | B2* | 10/2010 | Kawai | G02B 27/646 348/208.11 |
| 7,866,829 | B2* | 1/2011 | Takeuchi | G03B 9/02 353/88 |
| 8,192,346 | B2* | 6/2012 | Kawano | A61B 1/00158 600/9 |
| 8,248,204 | B2* | 8/2012 | Takeshima | G01V 15/00 340/10.1 |
| 8,378,967 | B2* | 2/2013 | Noda | G06F 3/038 178/18.07 |
| 8,821,015 | B2* | 9/2014 | Stagnitto | A61B 6/4291 378/205 |
| 8,863,749 | B2* | 10/2014 | Gooding | A61F 9/00827 128/898 |
| 9,103,916 | B2* | 8/2015 | Waters | G01S 19/48 |
| 9,141,194 | B1* | 9/2015 | Keyes | G06F 3/017 |
| 9,237,967 | B2* | 1/2016 | Gooding | A61B 3/102 |
| 9,336,477 | B2* | 5/2016 | Nitta | G06K 19/07762 |
| 9,358,157 | B2* | 6/2016 | Rathjen | A61F 9/00825 |
| 9,615,972 | B2* | 4/2017 | Shibata | A61F 9/00825 |
| 9,679,235 | B2* | 6/2017 | Sugar | G06K 19/0702 |
| 9,704,003 | B1* | 7/2017 | Anderson | G06K 7/10366 |
| 9,841,507 | B2* | 12/2017 | Waters | G01S 19/48 |
| 9,874,641 | B2* | 1/2018 | Waters | G01S 19/48 |
| 10,043,125 | B2* | 8/2018 | Park | G06K 19/07762 |
| 10,117,740 | B1* | 11/2018 | Lee | A61F 2/1624 |
| 2006/0280360 | A1* | 12/2006 | Holub | G01J 3/02 382/162 |
| 2008/0114314 | A1 | 5/2008 | Muehlhoff et al. | |
| 2008/0234707 | A1 | 9/2008 | Muehlhoff et al. | |
| 2008/0297291 | A1* | 12/2008 | Kawano | A61B 1/00158 335/285 |
| 2009/0234335 | A1* | 9/2009 | Yee | A61F 9/00829 606/5 |
| 2010/0188216 | A1* | 7/2010 | Nielsen | G01V 3/081 340/540 |
| 2010/0220054 | A1* | 9/2010 | Noda | G06F 3/014 345/156 |
| 2010/0253476 | A1* | 10/2010 | Poutiatine | A61J 7/0053 340/10.1 |
| 2011/0017222 | A1* | 1/2011 | Li | A61N 2/06 128/899 |
| 2012/0172126 | A1* | 7/2012 | Padovani | G06F 3/011 463/36 |
| 2012/0230473 | A1* | 9/2012 | Stagnitto | A61B 6/4291 378/205 |
| 2013/0226160 | A1* | 8/2013 | Rathjen | A61F 9/00825 606/4 |
| 2013/0293416 | A1* | 11/2013 | Waters | G01S 19/48 342/357.31 |
| 2015/0106373 | A1* | 4/2015 | Haverinen | G06F 16/285 707/737 |
| 2015/0206044 | A1* | 7/2015 | Nitta | G06K 19/07762 235/492 |
| 2016/0292563 | A1* | 10/2016 | Park | G06K 19/07762 |

OTHER PUBLICATIONS

Hae et al. "Using RFID for Accurate Positioning" Journal of Global Positioning Systems 2004 vol. 3, No. 1-2:32-39 (pdf attached) (Year: 2004).*

International Search Report and Written Opinion for Application No. PCT/IB2018/057805, dated Jan. 3, 2019, 13 pages.

* cited by examiner

OPHTHALMIC DOCKING SYSTEM WITH 3-DIMENSIONAL AUTOMATIC POSITIONING USING DIFFERENTIAL RF COUPLING

BACKGROUND OF THE INVENTION

Field of the Invention

This invention relates to docking of an instrument head to a patient interface device during laser ophthalmic surgery, and in particular, it relates to devices, system and method that aid automatic docking based on automatic positioning using differential RF coupling between the instrument head and the patient interface device.

Description of Related Art

Significant developments in laser technology have led to its application in the field of ophthalmic surgery, and laser surgery has become the technique of choice for ophthalmic surgical applications. Ophthalmic surgery is a precision operation and requires precise coupling between the surgical tool (i.e., the laser beam) and the region to be surgically altered (i.e., a portion of the patient's eye). Movement of the eye with respect to the intended focal point of the laser beam can lead to non-optimal results and could even result in permanent damage to tissue within the eye. Given that eye movement is often the result of autonomic reflex, techniques have been developed in an attempt to stabilize the position of a patient's eye with respect to an incident laser beam.

Mechanical stabilization devices, referred to as patient interfaces (PI), have been developed for coupling the patient's eye to the laser system. A PI typically has a component that directly contacts the eye, and engages and stabilizes the eye; meanwhile, the PI is attached to the laser system, so that the laser beam can be aligned to the eye. Currently available designs of PIs typically have either a single-piece or a two-piece structure.

Using a two-piece structure, the surgeon installs a lens cone on the beam delivery head of the laser system, and installs a suction ring assembly on the patient's eye using a suction force, and then docks the two pieces (lens cone and suction ring assembly) together using the motorized gantry of the laser system. In a single-piece structure, the lens cone and the suction ring assembly are integrated as one piece. In some systems that use a single-piece PI, the surgeon first installs the PI on the patient's eye, and then brings the laser head to the vicinity of the PI using the motorized gantry, and docks the laser head with the PI. A single-piece PI, or the piece of a two-piece PI that contacts the eye, is typically a single-use item intended to be used only once.

SUMMARY

Embodiments of the present invention provide an RF positioning system and related method for automated or assisted eye-docking in ophthalmic surgery. The system includes an RF detector system provided on the laser head and an RFID (Radio-frequency identification) tag provided on the PI.

Advantages of embodiments of the present invention include: Automation or assistance of eye docking in the treatment workflow enhances the alignment accuracy and also shortens the treatment time. Both will improve the diagnostic and treatment outcome. The shortened treatment time also contributes to patient comfort.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides an ophthalmic surgical laser system, which includes: a laser delivery head, including optics which define an optical axis for delivering a laser beam to an eye of a patient; an RF (radio frequency) detector system, which includes a first, a second, a third and a fourth RF antenna and a control device electrically coupled to the first through fourth antennas, wherein the first through fourth antennas are affixed on the laser delivery head and located in a plane perpendicular to the optical axis, wherein the first and second antennas have identical structures and are located at equal distances from the optical axis along a first line that passes through the optical axis, wherein the third and fourth antennas have identical structures and are located at equal distances from the optical axis along a second line that passes through the optical axis, and wherein the control device is configured to control each of the first through fourth antennas to measure an RF signal generated by an external RF antenna, and based on the measured RF signals by the first through fourth antennas, to determine whether or not the external RF antenna is located within a predetermined distance from the optical axis.

In another aspect, the present invention provides a patient interface device for use in ophthalmic surgery, which includes: a body having a round shape and defining a central area for accommodating an optical path of a laser beam; an annular flexible skirt located at a lower end of the body; and an RF (radio frequency) antenna having a ring shaped coil disposed on the body, the coil being centered on a rotational axis of the body.

In another aspect, the present invention provides a method for docking an ophthalmic surgical laser system to a patient's eye, the laser system including a laser delivery head which defines an optical axis for delivering a laser beam into the patient's eye, a mechanical structure configured to move the laser delivery head, and an RF (radio frequency) detector system, the RF detector system including first to fourth RF antennas and a control device, wherein the first through fourth antennas are affixed on the laser delivery head and located in a plane perpendicular to the optical axis, the first and second antennas have identical structures and are located at equal distances from the optical axis along a first line that passes through the optical axis, and the third and fourth antennas have identical structures and are located at equal distances from the optical axis along a second line that passes through the optical axis, the method including: (a) controlling each of the first through fourth antennas to measure an RF signal generated by an external RF antenna; (b) based on the measured RF signals by the first through fourth antennas, determining whether or not the external RF antenna is located within a predetermined distance from the optical axis; and (c) based on the measured RF signals by the first through fourth antennas, controlling the mechanical structure to move the laser delivery head toward the external RF antenna.

It is to be understood that both the foregoing general description and the following detailed description are exemplary and explanatory and are intended to provide further explanation of the invention as claimed.

DETAILED DESCRIPTION OF PREFERRED EMBODIMENTS

Eye docking is a critical first step in many ophthalmic diagnostic and treatment procedures. Currently all known eye docking systems require manual manipulation of the instrumentation head (e.g. laser head) in three dimensions to align the instrumentation head to the PI piece that is installed on the eye. The manipulation is typically performed using joystick or other input devices, either real or virtual, with the aid of a video camera. The feedback to the surgeon is the image showing the eye and parts of the laser head, which requires manual interpretation. This alignment requires dexterity and careful attention by the surgeon. Inexperience can significantly prolong the overall treatment time and add to patient discomfort. In current procedures, the only registration automation occurs after the eye is docked in place, i.e., after the laser head is coupled to the PI and the optical imaging system within the laser head is able to acquire images of the eye through the PI.

Embodiments of the present invention provides an RF positioning system and related methods that aid automatic docking in the "mid-range" of the overall eye registration operation, i.e., after the laser head is brought to within, for example, approximately 1 foot (approximately 30 cm) of the PI piece that has been installed on the eye, and before the laser head is sufficiently aligned and close to the PI piece such that the optical imaging system within the laser head is able to acquire images of the eye through the PI. Embodiments of the invention provide for automatic detection of relative position of the laser head with respect to the PI piece when they are within the operating range of approximately 1-2 feet from each other; the relative position information is used to automatically, without operator intervention, move the laser head toward the PI piece until the laser head is within a sufficiently close distance to the PI piece in at least the transverse directions (directions perpendicular to the optical axis of the laser head), e.g. within 2 mm or within 1 mm. Position detection is accomplished using differential RF (radio frequency) coupling.

Figure 1:
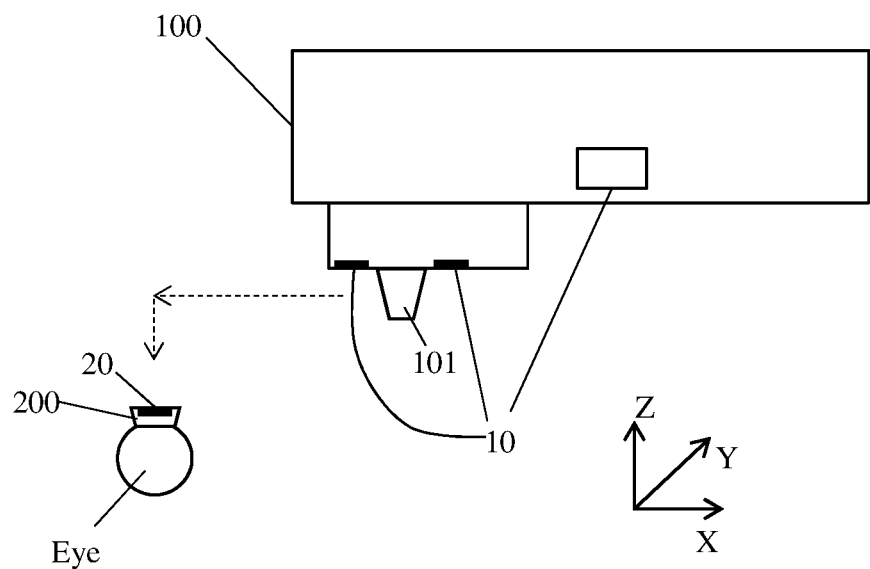
FIG. 1 schematically illustrates an ophthalmic surgical laser system incorporating an RF detector system for automatic or assisted eye docking according to an embodiment of the present invention.

More specifically, as schematically illustrated in FIG. 1, the RF positioning system includes an RFID tag 20 provided on the PI piece 200 that is mounted on the patient's eye, and an RF detector system 10 with multiple RF antennas provided on the laser head 100 to transmit RF signal to the RFID tag and detect the return signal generated by the RFID tag. The RF signals detected by the multiple RF antennas are used to determine or estimate the 3D position of the RFID tag and to move the laser head toward the PI piece. The laser head 100 includes mechanical structures controlled by a controller to move the laser head in X, Y and Z directions. Note that the illustration in FIG. 1 is highly schematic and is not intended to represent the actual shape, size, proportion, or precise physical location of the various components.

Embodiments of the present invention are applicable to both a laser ophthalmic surgery system that employs a two-piece PI, where the RFID tag is provided on the PI piece that is installed on the eye, and to a laser ophthalmic surgery system that employs a single-piece PI, where the RFID tag is provided on the PI and the PI is installed on the eye before it is docked to the laser head. In the descriptions herein, for convenience, the PI piece that has the RFID tag provided on it is referred to as "the PI" 200 for both types of systems.

An RFID tag modulates a switch across its receiving coil, which presents a variable RF signal that is detected by the RF detector antenna as 1 and 0 bits as the switch is opened and closed. The digital data contained in the serial bitstream is used as an ID code in a typical RFID system. In embodiments of the present invention, the RF detector system utilizes information contained in the analog amplitude of the on-off signal received by the detector, which is a function of the distance between the antenna of the RFID tag and the antenna of the RF detector as well as their relative orientation.

Preferably, in embodiments of the present invention, the RF signal strength used for positioning is derived from the high and low levels of the modulated RF signal generated by the RFID. For example, it may be calculated as the ratio of the difference of the high and low signal levels to the average of the high and low signal levels. Using the modulated high and low levels of the RF signal helps to increase the accuracy of the system, because the absolute amplitude of the RF signal may be prone to influence by external factors such as nearby objects which may reflect RF signals.

The RFID tag provided on the PI may be either a passive RFID tag, which does not contain a battery and operates on the received RF energy, or an active RFID tag with its own power source. Passive RFID tags require fewer components to be provided on the PI and are less expensive, which can reduce the additional cost of the PI (a disposable item), but active RFID tags provide much better RF signals which results in higher precision of position determination. RFID tags are well known and are commercially available. Any suitable RFID tags may be used to implement embodiments of this invention.

The RF detector system located on the laser head employs active components; it includes multiple antennas each transmitting RF signals to and receiving RF signals from the RFID tag. The RF detector system also includes a control device (which may include hardware circuits, a processor with memory storing computer programs, or other types of circuitry) for controlling the RF antennas and processing the signals received by them, as well as a power source. The RF antennas may have any suitable structure, and many such antennas are known and commercially available. The antennas are located at fixed locations on the laser delivery head. For example, the laser head may have a bottom surface from which a cone shaped housing 101 (see FIG. 1) protrudes; the antennas may be mounted on the bottom surface around this housing. Based on the relative signal strengths, and preferably also phase differences, of the RF signals transmitted by the RFID tag and received by different antennas of the RF detector, the control device determines the relative location of the RFID tag with respect to the RF antennas, and accordingly controls the movement of the laser delivery head to center it relative to the PI for docking to the PI.

Figure 2:
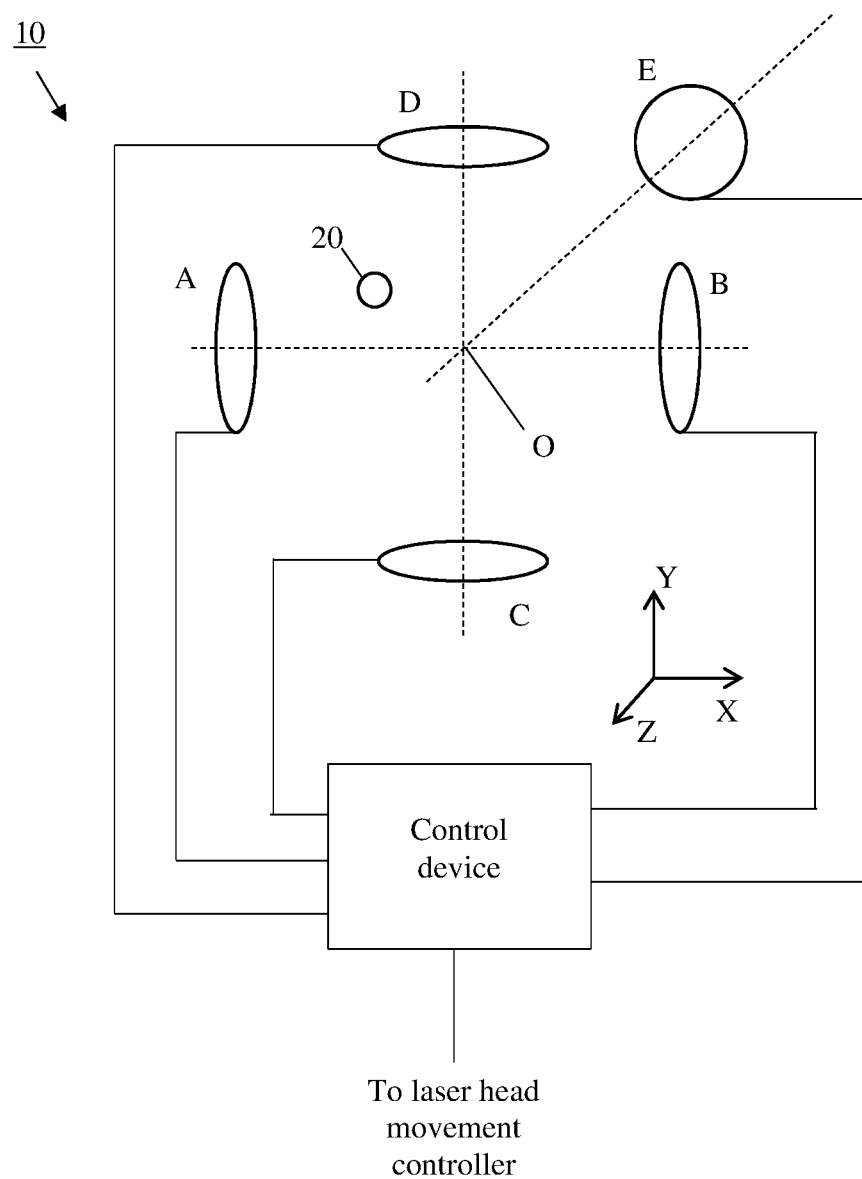
FIG. 2 schematically illustrates the structure of the RF detector system according to an embodiment of the present invention.

In one embodiment, schematically illustrated in FIG. 2, the RF detector system employs five RF antennas A-E. Four of the antennas A, B, C and D are identical in structure and located in an X-Y plane (horizontal plane which is perpendicular to the optical axis of the laser head) at the same distance from a center position O in the −X, +X, −Y and +Y directions, respectively. The distance from the center may be in the range of 1 to 100 cm, preferably 5 to 20 cm, more preferably about 10 cm. As will be discussed later, other antenna configurations are possible. The fifth antenna E is located above or below the X-Y plane. For example, the fifth antenna E may be located within or on the housing 101 (see FIG. 1). The fifth antenna E is optional. The center position O is the intersection of the X-Y plane and the optical axis of the laser beam to be delivered to the eye, which also corresponds to the intended docking position of the PI; i.e., the PI is deemed to be correctly docked when the RFID tag is located at the position (0, 0, −z) in the X-Y-Z coordinate system, Z being the vertical direction and parallel to the optical axis of the laser head. FIG. 2 schematically shows the RF tag 20 being at an off-centered position.

When the RFID tag is located between the antennas A and B in the X direction, the relative signal strengths, and preferably also the phase difference, of the RF signals detected by antennas A and B are used by the control device to determine the position of the RFID tag along the X axis. Likewise, when the RFID tag is located between the antennas C and D in the Y direction, the relative signal strengths, and preferably also the phase difference, of the RF signals detected by antennas C and D are used by the control device to determine the position of the RFID tag along the Y axis. The RF tag is deemed to be centered in the X-Y directions when the RF signals detected by the antennas A and B are of equal strengths and their phase difference is zero, and the RF signals detected by the antennas C and D are of equal strengths and their phase difference is zero. The signal strength of the RF signal detected by the fifth antenna E relative to the average signal strength of the in-plane antennas A to D is used by the control circuitry to determine the relative position of the RFID tag along the Z axis. The relative signal strength of the antenna E that corresponds to the correctly docked position of the PI may be established empirically.

Here, those skilled in the art would appreciate that when two quantities are said to be equal or their differences are said to be zero, what is meant is that their difference is less than a threshold which may depend on noise level in the signal and instrument limitations.

As the goal of the RF positioning system is to accurately and precisely center the RFID tag at the center position O defined by the multiple antennas of the RF detector, it is in fact not critical to precisely determine the position of the RFID tag when it is at an arbitrary off-centered position; what is important is to determine whether the RFID tag is precisely centered. As pointed out above, whether the RFID tag is centered can be determined by whether the signal strengths and phases of the two RF signals detected by antennas A and B, and by antennas C and D, are respectively equal to each other. By using the multiple antenna A-D in the configuration described above, the precision of the position centering within 2 mm or better can be achieved. In some embodiments, a precision of 1 mm or better can be achieved, in particular when an active RFID tag is used. In other words, the RF detection system is able to determine whether the RFID tag is located at within 1 or 2 mm or less from the center position O defined by the multiple antennas (i.e. from the optical axis of the laser head).

Thus, when the RF tag is at a location relatively far away from the center position, 1-2 mm level of precision is not required; it is sufficient for the RF detector to determine the approximate position of the PI or the approximate direction (in the X-Y plane) that the laser head needs to be moved in order to move it toward the PI. The position determination method therefore does not need to use a triangulation or multilateration algorithm.

The RF positioning system is also able to estimate the approximate position of the PI when the PI is located outside of the square region bound by the four antennas A-D. Outside of this region, the RFID tag will not be located between the antennas A and B, or between C and D, in the X and Y directions respectively, but the relative strengths and phase difference of the RF signals can still be used to estimate the approximate position of the PI or the approximate direction (in the X-Y plane) that the laser head needs to be moved in order to move it toward the PI. Even when the RF positioning system can only estimate an approximate position of the PI, it can achieve the goal of moving the laser head toward the PI. For example, if the phase difference between two RF signals from a pair of antennas (A and B, or C and D) is greater than a certain value, it may indicate that the PI is outside the region bound by the pair of antennas. When the signal strengths of both of the two RF signals increase when the laser head moves in a certain direction, it will indicate that the laser head is moving toward the PI. Thus, a trial and error approach may be used to move the laser head toward the PI when the PI is initially located too far from the center position.

In some embodiments, the operating range of the RF positioning system, i.e. the farthest distance of the RFID tag from the center position O of the RF detector such that the system can reliably operate to bring the laser head toward the PI, is approximately 1 foot (30 cm) or more. An operating range of 1 foot is sufficient for the purpose of automated docking, i.e., the surgeon only needs to manually move the laser head to within 1 foot from the PI.

During automated eye docking, the RF positioning system controls the movement of the laser head via a laser head movement controller. In a preferred embodiment, the laser head is initially position at a height above the PI, and controlled by the RF positioning system to automatically move in the horizontal (X-Y) plane first to center it above the PI, and then controlled to move in the vertical (Z) direction to lower it to dock with the PI. The RF positioning system may control the movement of the laser head using various modes, including continuous, stepwise, trial and error, etc., or combinations thereof. In a continuous mode, the laser head is controlled to move continuously in one direction in the X-Y plane, and the RF detector system continuously monitor the RF signals from the multiple antennas A-D to provide feedback signals to maintain or change the movement speed and/or direction. In a stepwise mode, the RF signals from the antennas A-D are measured and evaluated to estimate a horizontal direction of movement that will bring the laser head closer to the PI; the laser head is controlled to move in that direction by a certain amount (without continuous monitoring of the RF signals); and the RF signals from the antennas A-D are measured again and evaluated to determine the next step of movement. In a trial an error mode, which may be employed when the laser head is located a relatively far away from the PI, the initial movement may be in an arbitrary direction, and the RF signals are measured both before and after the initial movement to determine whether or not the laser head has been moved in the correct direction. In all of these modes or their combination, the movement stops when the laser head reaches the center position as determined based on the RF signals from the multiple antennas A-D.

After the laser head is centered above the eye, it is controlled to move downwards to dock with the PI, as schematically shown by the dashed-line arrows in FIG. 1. As mentioned earlier, the RF signal strength detected by the fifth antenna E relative to the average signal strength of the in-plane antennas A to D may be used to determine the relative position of the RFID tag along the Z axis, and control the downward movement of the laser head. Also as mentioned earlier, the fifth RF antenna E is optional. When the fifth antenna is not used, the final docking movement in the Z direction may be manually controlled, or controlled by other feedback systems.

The multiple antennas of the RF detector system may be operated in different modes. In some embodiments, the five antennas A, B, C, D and E (if present) are operated sequentially and the sequence is repeated, so only one of the antennas is transmitting and receiving RF signal at any moment in time. The RF control circuit is multiplexed among the multiple antennas sequentially, i.e., the control circuit controls the multiple antennas one at a time. This operation mode may be used when the laser head is not moving, or when the laser head is moving but the RF data acquisition is sufficiently fast such that the laser head has not moved appreciably during one round of RF measurement by the different antennas. In other embodiments, the five antennas may be operated to detect RF signals simultaneously. In yet other embodiments, one antenna (for example antenna E, or any one of A to D) is controlled to transmit RF signal while two or more other antennas (for example antennas A and B, or C and D) are controlled to receive the RF signals from the RFID tag simultaneously. The control device for the RF detector system can be configured accordingly to implement these modes of operation.

In addition to the antenna configuration shown in FIG. 2 and described above, other antenna configurations may be used. For example, in one alternative configuration, antennas A and B are at equal distance from the center O, and antennas C and D are at equal distance from the center O, but the distance from antenna C (and D) to the center O is different from the distance from antenna A (and B) to the center O. In another alternative configuration, the second pair of antennas C and D are not located along the Y axis, but are located along a line in the X-Y plane that passes through the center O but is at a non-orthogonal angle with respect to the X axis. In yet another alternative configuration, antennas A and B have identical structures (such as the shape, size, and the number of turns of the coil, etc.) and antennas C and D have identical structures, but antennas C and D have a different structure than antennas A and B.

Some other alternative antenna configurations may use fewer or more than four in-plane antennas, such as three or six (forming a hexagon, including three pairs of opposing antennas). Depending on the number and locations of the multiple antennas, position determination based on the relative signal strengths and phase differences may be more complex than that using the configuration of FIG. 2. One method for position determination is to calibrate the system beforehand, by recording the relative signal strengths and phase differences among the antennas at multiple known PI locations (e.g. a grid of locations). A lookup table (LUT) may be constructed, and then used to estimate the location of the PI and to move the laser head toward the PI.

Figure 3:
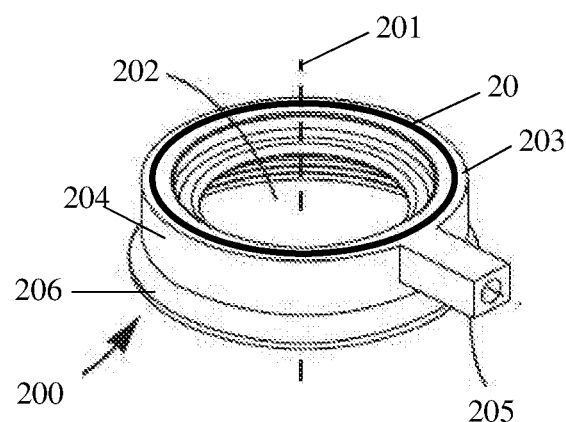
FIG. 3 schematically illustrates a patient interface incorporating an RFID tag according to an embodiment of the present invention.

As shown in FIG. 3, the antenna 20 of the RFID may be provided on the PI 200 at any suitable location. The PI typically has a round shape, such as a ring, a truncated cone, etc. The RFID tag is preferably locate on the PI such that its antenna is centered on the rotational axis 201 of the PI. Because the antenna is typically a ring shaped coil, it can be centrally position on the PI without obscuring a central area 202 that accommodates the optical path of the laser beam. For example, the antenna coil 20 may be located near an upper rim 203 of the PI as shown in FIG. 3, or on a side wall 204 of the PI, or near a lower end of the PI, etc. The antenna may be formed directly on or integrally with the PI, such as by printing or overmolding, or formed separately and then attached to the PI such as by an adhesive. If the RFID tag is an active device, the battery and other circuitry may be located at any convenient location of the PI, for example, on the handle 205. FIG. 3 also illustrates a flexible skirt 206 located at the lower end of the PI 200, configured to contact the anterior surface of the patient's eye when the PI is mounted on the eye.

The signal strength from the RFID tag as detected by each antenna of the RF detector on the laser head may be dependent on the orientation of the antenna of the RFID tag and the orientation of the antenna on the laser head. The above-described centering algorithm is applicable as long as the antenna of the RFID tag has a symmetrical round shape and the each pair of antennas on the laser head (A and B, and C and D, respectively) are symmetrically oriented with respect to the plane that passes through the center position O and is perpendicular to the line between the pair of antennas. It should be noted that while the antennas A-D are said to be located in the X-Y plane, they do not have to be oriented parallel to that plane; what is meant is that their centers are located in the same horizontal plane.

In an alternative embodiment, the RFID tag on the PI is replaced with a simple coil. Such an RF coil works on the same principle of RF energy absorption varying with distance from the transmitting antennas of the RF detector, although the RF signal from the RF coil will be a continuous signal, rather than a modulated bitsteam as is the case for an RFID tag. Without a modulation signal, the amplitude of the RF return loss measured by an antenna of the RF detector would be subject to drift over time or be influenced by external factors such as the presence of nearly objects that may reflect the RF signal. Such signal strength variation may be compensated for by a signal level calibration based on the received signal amplitude from each of the multiple antennas.

The inventors have constructed a test system using two receiver antennas and demonstrated that it can achieve position determination of the RFID device within 1 mm, when the RFID device is located between the two antennas and slightly out of the plane of the antennas.

The test system used the following components:
- Antenna on PI: wire coil around PI laser aperture window
- RFID tag: one that transmits a continuous RF signal at 433.92 MHz
- Transmitter: RF Solutions QAM-TX2-433
- Battery: Energizer CR1220VP 3V coin cell, 12.5 mm diameter
- Receivers: 2× standard UHF TV preamp with ¼-wave antenna tuned for 433 MHz In addition to eye docking in ophthalmic procedures, the automated or assisted docking system according to embodiments of the present invention may be useful in any surgical or diagnostic instrumentation that requires alignment of the instrument to a specific body part, or other systems where one part is required to be physically aligned with another part.

It will be apparent to those skilled in the art that various modification and variations can be made in the automatic docking system using RF positioning and related method of the present invention without departing from the spirit or scope of the invention. Thus, it is intended that the present invention cover modifications and variations that come within the scope of the appended claims and their equivalents.

What is claimed is:

1. An ophthalmic surgical laser system comprising:
a laser delivery head, including optics which define an optical axis for delivering a laser beam to an eye of a patient; and
an RF (radio frequency) detector system, which includes a first, a second, a third and a fourth RF antenna and a control device electrically coupled to the first through fourth antennas,
wherein the first through fourth antennas are affixed on the laser delivery head and located in a plane perpendicular to the optical axis, wherein the first and second antennas have identical structures and are located at equal distances from the optical axis along a first line that passes through the optical axis, wherein the third and fourth antennas have identical structures and are located at equal distances from the optical axis along a second line that passes through the optical axis, and
wherein the control device is configured to control each of the first through fourth antennas to measure an RF signal, and based on the measured RF signals by the first through fourth antennas, to determine whether or not an external RF antenna that has generated the RF signal is located within a predetermined distance from the optical axis.

2. The ophthalmic surgical laser system of claim 1, wherein the control device determines that the external RF antenna is located within the predetermined distance from the optical axis when the measured RF signals by the first and second antennas are of equal strengths and their phase difference is zero and when the measured RF signals by the third and fourth antennas are of equal strengths and their phase difference is zero.

3. The ophthalmic surgical laser system of claim 2, wherein each of the first through fourth antennas is configured to measure high and low signal levels of the RF signal and the RF detector system is configured to derive respective strengths of the RF signal from the measured high and low signal levels of the RF signal.

4. The ophthalmic surgical laser system of claim 1, wherein the predetermined distance is 1 mm.

5. The ophthalmic surgical laser system of claim 1, wherein the first line and the second line are orthogonal to each other.

6. The ophthalmic surgical laser system of claim 5, wherein the first through fourth antennas have identical structures and are located at equal distances from the optical axis.

7. The ophthalmic surgical laser system of claim 1,
wherein the RF detector system further includes a fifth RF antenna located outside of the plane,
wherein the control device is further configured to control the fifth antenna to measure the RF signal, and
wherein the control device is further configured to determine, based on the measured RF signals by the first through fifth antennas, a relative position of the external RF antenna that generated the RF signal in a direction along the optical axis.

8. The ophthalmic surgical laser system of claim 1, wherein the control device is configured to move the laser delivery head based on the measured RF signals by the first through fourth antennas.

9. The ophthalmic surgical laser system of claim 8, wherein the control device is configured to move the laser delivery head toward the external RF antenna.

10. An ophthalmic surgical laser system comprising:
a patient interface device which includes:
a body having an annular shape and defining a central area for accommodating an optical path of a laser beam and a central axis within the central area;
an annular skirt located at one end of the body; and
an RF (radio frequency) antenna having a ring shaped coil disposed on the body along a perimeter of the annular shape and around the central area, the coil being centered on the central axis of the body;
a laser delivery head, including optics which define an optical axis for delivering a laser beam to an eye of a patient;
an RF detector system, which includes a first, a second, a third and a fourth RF antenna and a control device electrically coupled to the first through fourth antennas,
wherein the first through fourth antennas are affixed on the laser delivery head and located in a plane perpendicular to the optical axis, wherein the first and second antennas have identical structures and are located at equal distances from the optical axis along a first line that passes through the optical axis, wherein the third and fourth antennas have identical structures and are located at equal distances from the optical axis along a second line that passes through the optical axis,
wherein the RF antenna of the patient interface device is configured to generate an RF signal, and
wherein the control device is configured to control each of the first through fourth antennas to measure the RF signal, and based on the measured RF signals by the first through fourth antennas, to determine whether or not the RF antenna of the patient interface device is located within a predetermined distance from the optical axis.

11. The ophthalmic surgical laser system of claim 10, wherein the patient interface device further comprises circuitry disposed on the body, where the circuitry and the RF antenna forms an active RFID (Radio-frequency identification) device.

12. The ophthalmic surgical laser system of claim 10, wherein the patient interface device further comprises circuitry disposed on the body, where the circuitry and the RF antenna forms a passive RFID (Radio-frequency identification) device.

13. A method for docking an ophthalmic surgical laser system to a patient's eye,
the laser system comprising a laser delivery head which defines an optical axis for delivering a laser beam into the patient's eye, and an RF (radio frequency) detector system, the RF detector system including first to fourth RF antennas and a control device, wherein the first through fourth antennas are affixed on the laser delivery head and located in a plane perpendicular to the optical axis, the first and second antennas have identical structures and are located at equal distances from the optical axis along a first line that passes through the optical axis, and the third and fourth antennas have identical structures and are located at equal distances from the optical axis along a second line that passes through the optical axis, and wherein the control device is operatively coupled to the laser delivery head,
the method comprising:
(a) installing a patient interface device on the patient's eye, the patient interface device including an RF antenna configured to generate an RF signal;

(b) the control device controlling each of the first through fourth antennas to measure the RF signal generated by the RF antenna of the patient interface device;

(c) based on the measured RF signals by the first through fourth antennas, the control device determining whether or not the RF antenna of the patient interface device is located within a predetermined distance from the optical axis; and (d) based on the measured RF signals by the first through fourth antennas, the control device moving the laser delivery head toward the RF antenna of the patient interface device.

14. The method of claim 13, wherein step (c) includes: the control device determining that the RF antenna of the patient interface device is located within the predetermined distance from the optical axis when the measured RF signals by the first and second antennas are of equal strengths and their phase difference is zero and when the measured RF signals by the third and fourth antennas are of equal strengths and their phase difference is zero.

15. The method of claim 14, wherein step (b) includes the control device controlling each of the first through fourth antennas to measure high and low signal levels of the RF signal and deriving respective strengths of the RF signal from the measured high and low signal levels of the RF signal.

16. The method of claim 13, wherein the predetermined distance is 1 mm.

17. The method of claim 13, wherein the RF detector system further includes a fifth RF antenna located outside of the plane, wherein the method further comprises:

the control device controlling the fifth antenna to measure the RF signal generated by the RF antenna of the patient interface device; and based on the measured RF signals by the first through fifth antennas, the control device determining a relative position of the RF antenna of the patient interface device in a direction along the optical axis.

18. The method of claim 13, wherein in step (b) includes the control device controlling the first through fourth antennas to sequentially measure the RF signal generated by the RF antenna of the patient interface device.

19. The method of claim 13, wherein in step (b) includes either the control device controlling the first and second antennas to simultaneously measure the RF signal generated by the RF antenna of the patient interface device, or the control device controlling the third and fourth antennas to simultaneously measure the RF signal generated by the RF antenna of the patient interface device.

* * * * *